(12) United States Patent
Terwilliger et al.

(10) Patent No.: US 7,540,998 B2
(45) Date of Patent: Jun. 2, 2009

(54) DELIVERY SYSTEM AND PRESCRIPTION METHOD FOR INTERSTITIAL RADIATION THERAPY USING ENHANCED PARAMETRIC RELEASE STERILIZATION TECHNIQUES

(75) Inventors: Richard A. Terwilliger, Southbury, CT (US); Gary A. Lamoureux, Woodbury, CT (US)

(73) Assignee: Biocompatibles UK Limited, Famham, Surrey (GB)

( * ) Notice: Subject to any disclaimer, the term of this patent is extended or adjusted under 35 U.S.C. 154(b) by 889 days.

(21) Appl. No.: 10/987,141

(22) Filed: Nov. 12, 2004

(65) Prior Publication Data

US 2005/0191207 A1  Sep. 1, 2005

Related U.S. Application Data

(60) Provisional application No. 60/523,501, filed on Nov. 19, 2003.

(51) Int. Cl.
- *A61L 9/00* (2006.01)
- *A61N 5/00* (2006.01)
- *A61M 36/00* (2006.01)
- *A61M 31/00* (2006.01)

(52) U.S. Cl. .............................. 422/28; 422/1; 422/29; 422/30; 422/32; 422/34; 422/305; 600/1; 600/3; 600/7; 600/8; 604/48; 604/57; 604/59; 604/60

(58) Field of Classification Search .................... 422/1, 422/28–30, 32, 34, 305; 600/1, 3, 7–8; 604/48, 604/57, 59, 60
See application file for complete search history.

(56) References Cited

U.S. PATENT DOCUMENTS

| | | | |
|---|---|---|---|
| 3,476,506 A | 11/1969 | Anderson et al. | |
| 3,728,839 A * | 4/1973 | Glick | 53/425 |
| 4,203,943 A | 5/1980 | Gillis et al. | |
| 5,460,592 A * | 10/1995 | Langton et al. | 600/7 |
| 5,464,580 A * | 11/1995 | Popescu et al. | 422/34 |
| 5,928,130 A | 7/1999 | Schmidt | 600/7 |
| 5,938,583 A | 8/1999 | Grimm | 600/7 |
| 6,345,449 B1 * | 2/2002 | Lepore | 34/389 |
| 6,365,103 B1 * | 4/2002 | Fournier | 422/33 |
| 6,440,364 B1 * | 8/2002 | Vera et al. | 422/33 |
| 6,537,193 B1 | 3/2003 | Lennox | 600/3 |
| 2003/0063997 A1 * | 4/2003 | Fryer et al. | 422/3 |
| 2003/0138344 A1 * | 7/2003 | Mielnik et al. | 422/2 |
| 2003/0191355 A1 | 10/2003 | Ferguson | |

OTHER PUBLICATIONS

Int'l Search Report for PCT/US04/38647, May 18, 2005.

* cited by examiner

*Primary Examiner*—Jill Warden
*Assistant Examiner*—Monzer R. Chorbaji
(74) *Attorney, Agent, or Firm*—Fliesler Meyer LLP

(57) ABSTRACT

A process is provided for sterilizing brachytherapy devices with Ethylene Oxide gas and releasing the devices on a parametric release basis. Devices that can be sterilized with this process include interstitial radiation seed strand implants and the needles used for implantation. In order to be sterilized effectively by EtO gas, the devices are constructed such that surfaces not readily infused with EtO gas are made to be gas permeable, and will not retain the gas after the sterilization process. Performance qualification of the sterilization process is performed through physical and microbiological studies, and set of established physical process parameters. Maintaining the physical process parameters in subsequent sterilization cycles will consistently yield the desired sterility assurance level without having to test the devices for sterility.

39 Claims, 4 Drawing Sheets

DELIVERY SYSTEM AND PRESCRIPTION METHOD FOR INTERSTITIAL RADIATION THERAPY USING ENHANCED PARAMETRIC RELEASE STERILIZATION TECHNIQUES

CLAIM TO PRIORITY

The present application claims the benefit of priority under 35 U.S.C. § 119(e) to U.S. Provisional Application entitled: "DELIVERY SYSTEM AND PRESCRIPTION METHOD FOR INTERSTITIAL RADIATION THERAPY USING ENHANCED PARAMETRIC RELEASE STERILIZATION TECHNIQUES," Application No. 60/523,501 filed on Nov. 19, 2003, which application is incorporated herein by reference.

CROSS-REFERENCE TO RELATED APPLICATIONS

The following applications are cross-referenced and incorporated herein by reference as if fully set forth herein:

U.S. patent application Ser. No. 10/397,940, entitled, "Delivery System and Method for Interstitial Radiation Therapy," by Terwilliger et al., filed Mar. 26, 2003.

U.S. patent application Ser. No. 10/035,083, entitled, "Delivery System and Method for Interstitial Radiation Therapy," by Terwilliger et al., filed Dec. 28, 2001.

U.S. patent application Ser. No. 10/162,548, entitled, "Delivery System and Method for Interstitial Radiation Therapy Using Strands Constructed with Extruded Strand Housing," by Terwilliger et al., filed Jun. 4, 2002.

U.S. patent application Ser. No. 10/162,546, entitled, "System for Manufacturing Interstitial Radiation Therapy Seed Strands," by Terwilliger et al., filed Jun. 4, 2002.

U.S. patent application Ser. No. 10/162,006, entitled, "Delivery System and Method for Interstitial Radiation Therapy Using Strands Constructed with Extruded Strand Housings," by Terwilliger et al., filed Jun. 4, 2002.

FIELD OF INVENTION

The present invention relates to systems and methods for delivering a plurality of radioactive sources to a treatment site, and to methods for transporting and sterilizing such radioactive sources.

BACKGROUND

Brachytherapy is an advanced form of interstitial radiation cancer treatment, in which radioactive seeds or sources are placed in or near the tumor itself, delivering a high radiation dose to the tumor while minimizing the radiation exposure in the surrounding healthy tissues. There have been numerous developments in brachytherapy. For example, U.S. Pat. No. 4,402,308 to Scott describes a technique wherein a hollow metal needle is inserted into the tumor and the seeds are thereafter inserted into the needle. As the needle is retracted from the tissue, the seeds are deposited in the tumor at desired locations. The instruments disclosed in the '308 patent to Scott are difficult to manipulate, given that their overall length is over 20 cm, and they are relatively heavy.

Another disadvantage of the technique disclosed by the above-referenced patent is that the seeds are deposited in a track made by the needle. Specifically, when the needle is withdrawn from the tissue, the seeds tend to migrate in the track, resulting in a poor distribution of seeds. Poor seed distribution can result in undesirable concentration(s) of seeds, causing either an over-dosage or an under-dosage of radiation. Additionally, over time, the seeds tend to migrate along the needle track away from the tumor; accordingly, patients commonly must repeat the procedure within a couple of months to have seeds re-implanted near the tumor.

Recently, integrated elongated assemblies, or "seed strands," have been employed to introduce seeds into tumor sites. A pre-manufactured, elongated assembly or implant typically contains seeds that are spaced at 1 cm increments. The assembly is loaded into an introducer needle just prior to the implantation procedure.

There are many benefits to using seed strands in pre-implantation and post-implantation procedures. Seed strands are easier to handle and load into needles, since the strand structure eliminates the need to sort manually each seed and spacer. The "spacers" in the seed strands actually are integrated into the strand itself. Unlike loose seeds, which can migrate as the tumor grows or shrinks, a seed strand can maintain correct spacing between seeds even after being introduced into the body. The strands are sufficiently flexible and pliable to move with the tissue as the tissue shrinks back to pre-operative size. A seed strand also has sufficiently axial rigidity to allow easy expulsion of the strand from the implantation needle. In contrast, loose seeds have been known to jam inside an implantation needle.

A system for providing an elongated implant having radioactive seeds disposed therein is disclosed in U.S. Pat. No. 4,697,575 to Horowitz, which is incorporated herein by reference. In this system, a plurality of encapsulated radioactive seeds are positioned in a predetermined array. The seeds are encapsulated individually, with each capsule having a projection on one capsule end and a complementary recess on the remaining capsule end. A projection in one capsule is engageable with a recess in an adjacent capsule, such that the desired number of seeds can be plugged together to form a column of rigid, bio-absorbable and elongated material.

In another embodiment disclosed in the same patent, a rigid needle implant containing radioactive segments with break points is inserted into the tumor. The needle implant is made of a bio-absorbable polymer that is sufficiently rigid to be driven into the tumor without deflection and without use of a separate hollow needle. When the proper depth is reached with the rigid polymer needle, the remaining uninserted portion of the needle is broken off.

The above-referenced U.S. Patent Applications to Terwilliger and Lamoureux disclose additional seed strands, and are incorporated herein by reference. The seed strands comprise a bio-absorbable carrier material in the form of an elongated member with radioactive seeds disposed within the carrier material. The seeds are accurately spaced at a predetermined distance from one another, and maintain that spacing even after being introduced into the body. The elongated member is sufficiently axially rigid so as to maintain the spacing between seeds and to be easily injected into a tissue for treatment. The elongated member is also flexible and pliable enough to move with the tissue as the tissue shrinks back to pre-operative size. The devices can be used and placed with precision, and maintain their positions after the implantation, until the bio-compatible material dissolves and the seeds have become inert. The devices can be custom manufactured according to the pre-operative diagnosis for each patient, and as few as one patient's order can be manufactured at one time.

Before brachytherapy devices are shipped from the manufacturer, they must undergo rigorous sterilization. Sterilization methods include the use of steam sterilization, dry heat sterilization, radiation sterilization, gamma radiation, and chemical sterilization using agents such as hydrogen peroxide, chlorine dioxide, and ethylene oxide ("EtO").

The use of EtO, a flammable, colorless gas at temperatures above 51.3° F. (10.7° C.), is one of the most commonly used sterilization methods. EtO is a potent anti-microbial agent that kills all known viruses, bacteria, and fungi, and is used to process sensitive instruments which cannot be adequately sterilized by other methods. Approximately half of the medical devices in the United States are sterilized with EtO.

The typical EtO sterilization process includes initial inventory control checks, placement of bio-indicators ("BI"), preconditioning, time inside the sterilization vessel, aeration, retrieval of the BIs, shipment of BIs to the testing laboratory, BI preparation, and as many as seven days of BI incubation. A test result report then must be compiled and communicated to the manufacturer. Only then can the manufacturers arrange return shipment of the tested lot to the manufacturing site for inspection and distribution.

Typical EtO sterilization times by a third-party certified facility are 2 days for processing and 7-10 days for the sterilization to be certified by bio-indicators that are incubated and tested. A given product lot could spend up to 11 days at a contract EtO facility, and even longer if weekends and holidays are taken into account. This turnaround time might be acceptable for most medical devices, and the price considered cost-effective for volume sterilization. However, for pre-packaged, radioactive delivery systems such as brachytherapy devices, time is of the essence. The period between the ordering of seeds to implanting them in the patient optimally should be as short as possible because the radioactivity of the seeds used in implants decays at a daily rate of about 3%, and because aggressive tumor growths should be treated with minimal delay.

To account for the additional time needed for sterilization, radioactive seeds used in interstitial radiation therapy are typically made "hotter" (i.e., more radioactive) than necessary when manufactured with the expectation that the seeds will have decayed to the proper activity level at the time of implantation. "Hotter" seeds are more expensive, and their use must be carefully monitored to ensure that the patient receives the precise dosage of radiation.

Further, since each implant can be custom-made according to each patient's pre-operative diagnosis and implantation may be required at any time, there is a need to economically sterilize as few as one patient's order as quickly as possible. Sterilization done at an outside facility would be cost-prohibitive because there is inadequate volume to spread the cost. Further, in most cases the devices cannot be sterilized along with other medical products because of differing pre-set sterilization requirements for the devices. The cost of sterilizing one patient's order would therefore bear the entire lot charge cost of a sterilization cycle.

It is possible to shorten the time and reduce the cost of sterilization by releasing sterilized devices based on "parametric release." Parametric release is the release of sterilized products based on a declaration that the routine sterilization process performed is adequate, based solely on measurement and documentation of physical process parameters rather than the results of bio-indicators or product sterility evaluations. In other words, utilization of parametric release can avoid the costs and delays associated with incubating and testing with BIs.

EtO parametric release can be defined as a protocol that has been sufficiently tested to assure a kill rate of $10^{-6}$ Sterility Assurance Level ("SAL"), with an allowable EtO residual measurement after the sterilization cycle. Medical device manufacturers and sterilization contractors must validate the sterilization process in order to provide documented evidence that it will consistently yield the desired SAL. Upon completing all stages of validation, routine control procedures are established for subsequent cycles, which consist of monitoring the physical parameters of the process. The sterilized products may be released upon confirmation that the routine production cycle has fallen within the parameters established during validation. In other words, sterility testing on the actual finished products can be reduced or even eliminated.

DESCRIPTION OF THE DRAWINGS

The embodiments of FIGS. 1A and 1B represent a delivery system and method for interstitial radiation therapy

The embodiments of FIGS. 2A through 2B represent a tray for sterilization and transportation of the therapeutic implant shown in FIGS. 1A -1B.

The embodiment of FIG. 3 shows the detail of how a needle is loaded in the tray depicted in FIG. 2A.

The embodiment of FIG. 4 shows the detail of how sterilized product is shipped in the tray depicted in FIG. 2A.

DETAILED DESCRIPTION OF THE PREFERRED EMBODIMENT

For the purposes of this Patent application, the following definitions apply.

Aeration: Part of the sterilization process during which ethylene oxide and/or its reaction products desorb from the medical device until predetermined levels are reached. Aeration may be performed within the sterilizer and/or in a separate chamber or room.

Aeration area: Either a chamber or a room in which aeration occurs.

Bioburden: Population of viable microorganisms on a raw material, component, finished product, and/or package.

Biological Indicator ("BI"): Inoculated carrier contained within its primary pack providing a known resistance to the relevant process.

Chamber: Enclosed area that accommodates only sufficient product to fill the sterilizer.

Conditioning: Treatment of product within the sterilization cycle, but prior to sterilant admission, to attain a predetermined temperature and relative humidity. This part of the sterilization cycle may be carried out either at atmospheric pressure or under vacuum.

D-value: Time required to achieve inactivation of 90% of a population of the test microorganism under stated conditions.

Exposure time: Time for which the sterilizer chamber is maintained within the specified range for temperature, sterilant concentration, pressure, and humidity.

Flushing: Procedure by which the sterilant is removed from the load and chamber by either multiple alternate admissions of filtered air or inert gas and evacuations of the chamber, or continuous passage of filtered air or inert gas through the load and chamber.

Parametric release: The release of sterilized products based on a declaration that the routine sterilization process performed is adequate, based solely on measurement and documentation of physical process parameters rather than the results of bio-indicators or product sterility evaluations.

Performance qualification: Obtaining and documenting evidence that the equipment as commissioned will produce acceptable product when operated in accordance with the process specification.

Pre-conditioning: Treatment of product prior to the sterilization cycle in a room or chamber to attain specified limits for temperature and relative humidity.

Pre-conditioning area: Either a chamber or a room in which preconditioning occurs.

Process Challenge Device ("PCD"): Object that simulates the worst case of conditions as they are given for the sterilizing agent(s) in the items or the goods to be sterilized. The device is so constituted that a biological indicator can be arranged in the place most difficult for the sterilant to reach. The design of the process challenge device depends on the kind of goods to be sterilized and the sterilization procedure. The biological indicator should not interfere with the function of the process challenge device.

Process development: Documented program of studies that is performed in order to define the sterilization process based on the product/packaging/loading pattern and/or equipment limitations.

Reference load: Specified sterilization load made up to represent the most difficult combination of products to be sterilized.

Revalidation: Set of documented procedures to confirm an established validation.

Room: Enclosed area capable of holding more product than can be accommodated in the sterilizer(s) at any one time.

Sterile: Free from viable microorganisms.

Sterility: State of being free from viable microorganisms. In practice, no such absolute statement regarding the absence of microorganisms can be proven.

Sterility assurance level ("SAL"): Probability of a viable microorganism being present on a product unit after sterilization.

Sterilization: Validated process used to render a product free of all forms of viable microorganisms. In a sterilization process, the nature of microbial death is described by an exponential function. Therefore, the presence of viable microorganisms on any individual item can be expressed in terms of probability. Although this probability may be reduced to a very low number, it can never be reduced to zero. The probability can be expressed as a sterility assurance level. SAL is normally expressed as $10^{-n}$.

Sterilization cycle: Treatment in a sealed chamber comprising air removal, conditioning (if used), injection of sterilant, exposure to ethylene oxide, removal of ethylene oxide, and flushing (if used).

Sterilization load: Goods that are to be or have been sterilized simultaneously in the same sterilization chamber. The sterilization load may include more than one manufacturing batch or lot.

Sterilization process: All treatments that are required to accomplish sterilization, including preconditioning (if used), the sterilization cycle, and aeration.

Validation: Documented procedure for obtaining, recording, and interpreting the results needed to show that a process will consistently yield a product complying with predetermined specifications. Validation is considered as a total process that consists of commissioning and performance qualification.

Sterilization Process

The following discussion relates to the sterilization process for interstitial radiation brachytherapy devices. Exemplary devices include seed strand implants, and the needles used for implantation. The process is carried out using equipment qualified for EtO sterilization. The preferred embodiment uses EtO injected into a porous bag. Terms commonly used to described this process include "bag method," "gas diffusion method," "sterilization pouch," and "injection method." Examples of qualified equipment include the EOGas™ Sterilization System, by Andersen Products of Haw River, N.C. The EOGas™ Sterilization System utilizes a cartridge released EtO dose, custom designed sterilization bags to contain the items being sterilized, and an EOGas™ heated and ventilated sterilization cabinet.

Figure 1A:
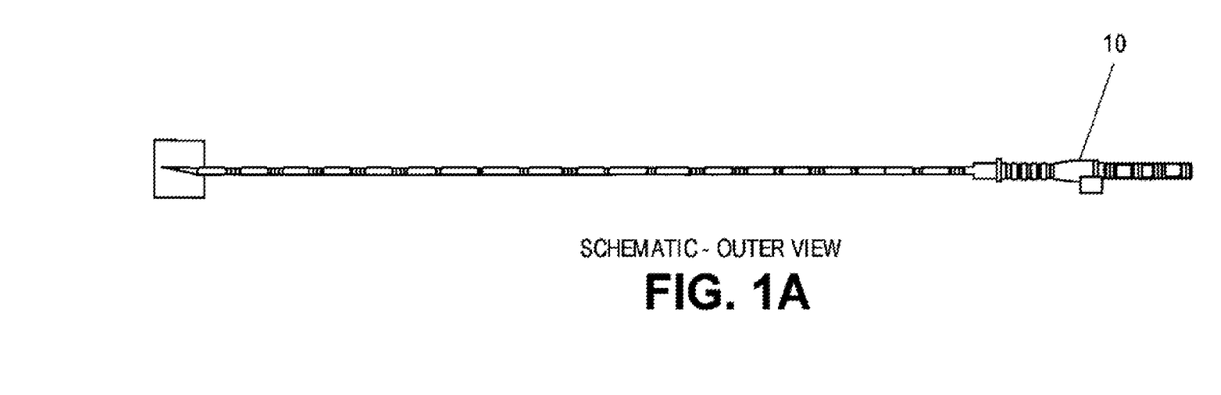
FIG. 1A is a schematic outer view of the brachytherapy device loaded into a needle.
Figure 1B:
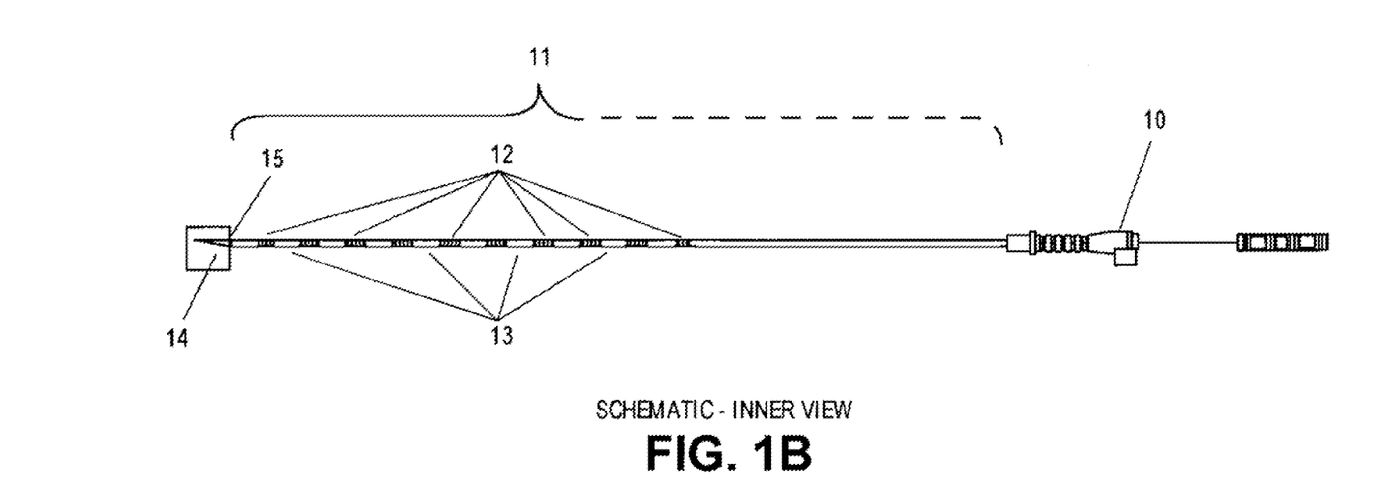
FIG. 1B is a schematic inner view of the brachytherapy device loaded into a needle.
Figures 2A, 2B:
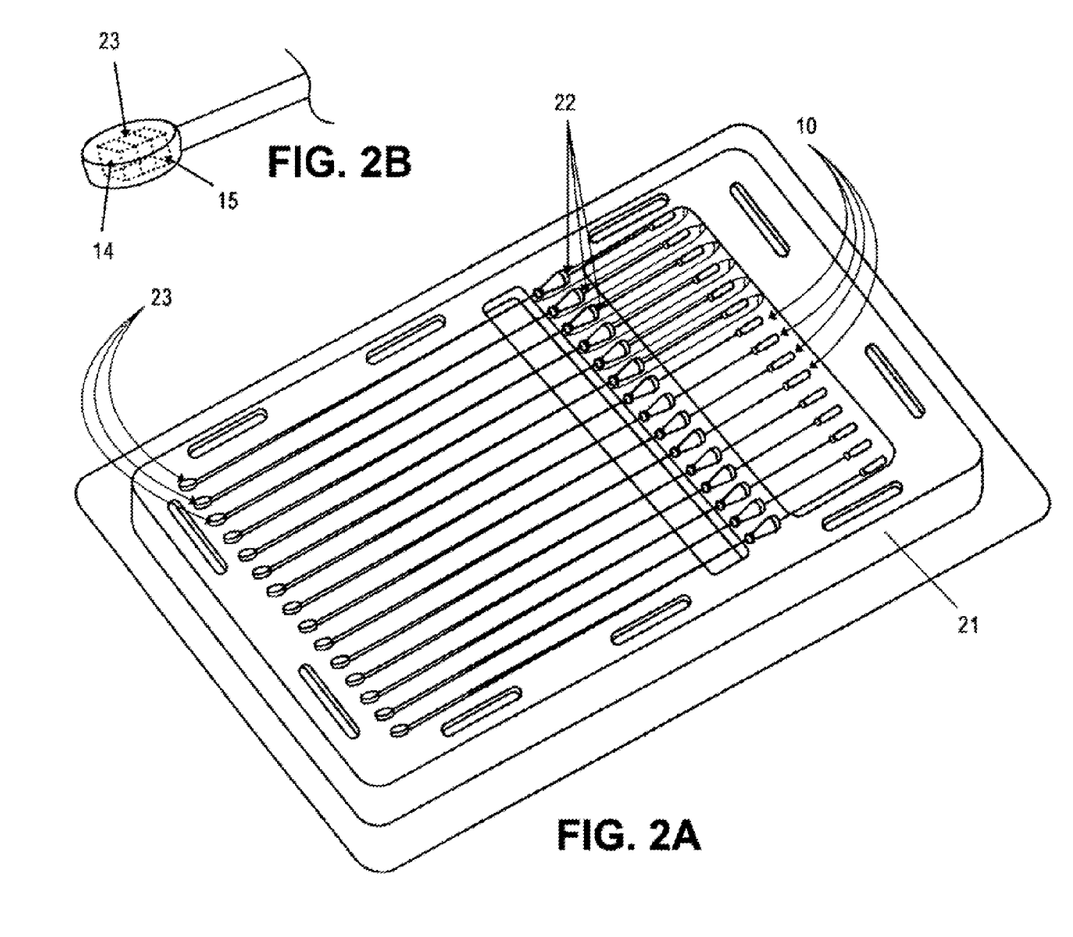
FIG. 2A is a view in profile of an embodiment of the tray for sterilizing and transporting a multitude of therapeutic strands loaded into needles.
FIG. 2B is an enlarged view of a needle tip and plug imbedded in dense closed cell foam.
Figures 3A, 3B:
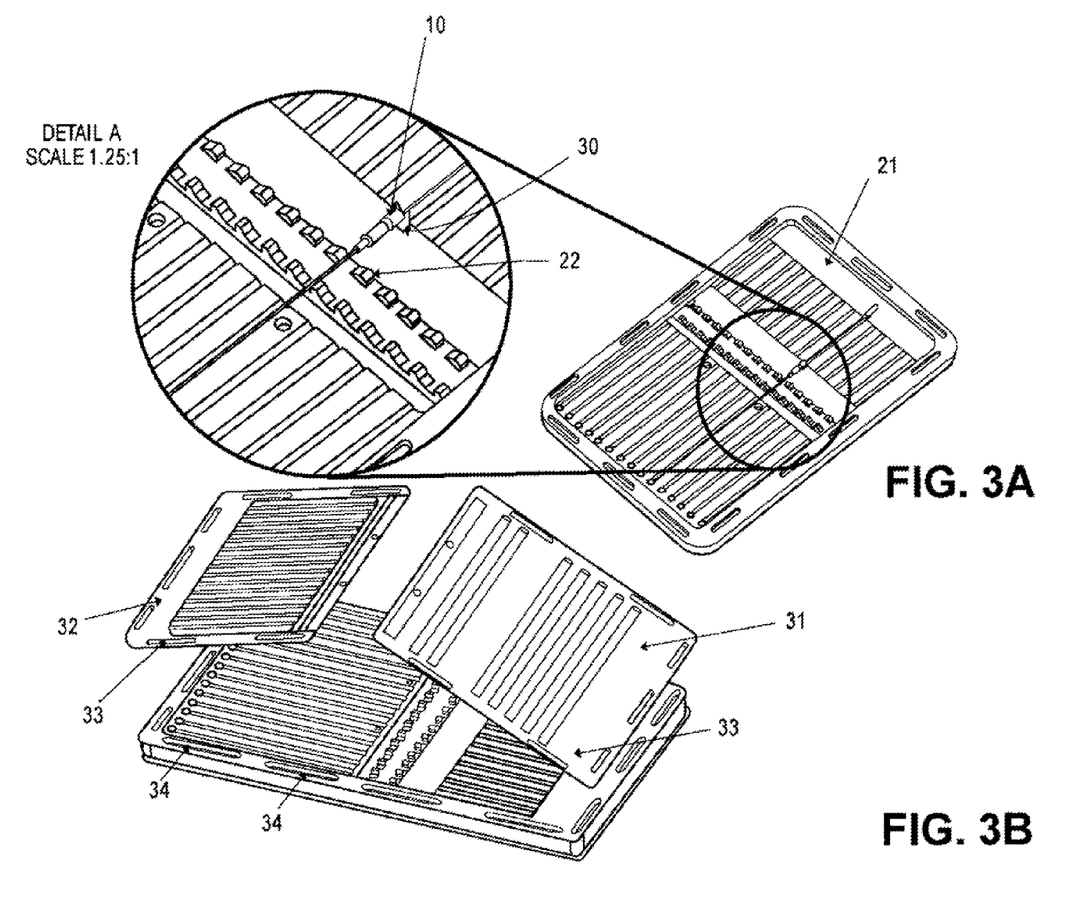
FIG. 3A is a close-up view of a needle being held in place in the tray of an embodiment of the invention.
FIG. 3B shows lids being fitted onto the tray of an embodiment of the invention.

Referring to FIG. 1A, a radioactive seed implant comprising an elongated member with seeds and spacers dispersed therein, is loaded into a needle. FIG. 1B shows an inner view of the loaded needle, showing the elongated member 11 with radioactive seeds 12 dispersed within the bio-absorbable material 13. The needle's tip 15 is fitted with a safety plug 14 made of gas-permeable materials. Thereafter, the loaded needles are placed in a specially designed tray 21, which holds a plurality of loaded needles 10. (FIG. 2A.) The tray has rows of straight walled "close fit" holders, into which a needle is placed and secured. (FIG. 3A). The pathways in the tray and the needles are designed so that all surfaces are reachable and can be sterilized by EtO gas.

The tray holds and prevents accident movements of the needle stylet (or "plunger"). A clip 30 locks the stylet from movement during handling, and is removed prior to implant. Referring to FIGS. 2A and 2B, the needle tips 15 with safety plugs 14 are embedded in dense, close cell foam cylinders 23 built into the trays to prevent any possible seed loss or contamination during shipping and handling.

Referring to FIG. 3, after the needles 10 are secured, tray lids 31, 32 are attached to the tray and locked into place by opposing tabs in the trays 34 and lids 33. The tray is then placed in a gas diffuser bag 41 made of a EtO gas permeable material, such as DUPONT's TYVEK®. The diffuser bags are sealed and then carefully loaded into a sterilization bag, such as Anderson Products' number 5 bag. The sterilization bag should also be gas permeable to EtO gas. A fully loaded sterilization bag can hold up to 8 gas diffuser bags loaded with trays.

Preconditioning of the sterilization chamber should be carried out prior to loading the trays. Preconditioning or conditioning may be performed in the sterilization chamber or in a separate preconditioning area (e.g., a chamber, cell, or room). The preconditioning area should have adequate air circulation to ensure the uniformity of temperature and humidity in the space. Monitors and controls for setting air circulation, temperature, and humidity in the room should be used. Load temperature recording probes should also be used continuously to monitor the load. The number of probes used in routine production should be sufficient to demonstrate that the prescribed load temperature range was maintained for the entire load. The time of load entry into, and removal from, the preconditioning area also should be recorded.

A source of EtO is provided and includes an EtO gas cartridge, which contains a measured unit dose of about 100% ethylene oxide. The cartridge, such as Andersen Products no. 5 EOGas™ cartridge, is placed directly into the interior of the sterilization bag together with the sealed gas diffusion bags. Air is evacuated from the sterilization bag and the bag thereafter is sealed to achieve a substantially leak-proof seal. The sealed sterilization bag subsequently is placed in a prewarmed sterilization chamber of the sterilization cabinet. The door of the sterilizer is closed and locked.

The sterilization chamber uses load temperature recording probes to continuously monitor the load. The number of probes used in routine production should be sufficient to demonstrate that the prescribed load temperature limits were maintained for the entire load. Typically, the number and placement of probes used during routine production can be determined on the basis of validation data. The chamber also should have independent systems for recording and controlling chamber pressure, chamber temperature, and chamber humidity, and instrumentation for analysis of humidity during conditioning and the EtO concentration during sterilant dwell time. Adequate circulation must be maintained to ensure the uniformity of temperature, humidity, and gas concentration within the chamber, which may be demonstrated by temperature, humidity profiles, and lethality mapping studies. Circulation systems may be used to achieve homogeneous conditions within the chamber. Finally, gas inlet temperature should be monitored.

The sterilization temperature, pressure, cycle times for sterilization, and purging are then set for the sterilizer chamber. Sterilization temperatures should be about 45° C. to about 55° C., and preferably about 50° C. The sterilization cycle operates for about 4 hours to about 16 hours at a pressure of about 0 to about 1 inch vac. The purge cycle operates for about 12 to 24 hours. The cycle times of the sterilization cycle and the purge cycle are chosen to ensure a sufficient amount of the EtO gas circulates or penetrates into the device and needles, and contacts substantially all surfaces.

As discussed above, the materials used to construct the elongated member of the device are chosen to be EtO gas permeable, and will not retain the gas when the gas is purged from the material after the sterilization cycle is complete.

Next, EtO gas is introduced into the sterilization bag to create the sterilizing atmosphere. The gas cartridge is activated without opening the sterilization bag by pressing a trigger located exterior to the sterilization chamber. The released EtO gas is heated to the set sterilization temperature to begin the sterilization cycle. As EtO is released from the cartridge, the gas molecules permeate throughout the sterilization bag and into the gas diffusion bags. Pathways in the trays allow the EtO gas to circulate and penetrate into the brachytherapy devices and needles. The seeds, which are covered by the polymeric material of the elongated member, are sterilized through gas permeating through the material itself. The elevated sterilization temperature maintained throughout the sterilization cycle helps to facilitate the circulating and penetrating action of the EtO gas molecules in the sterilization bag.

As EtO gas is released from the cartridge, it circulates throughout the gas diffusion bags and gradually diffuses through the walls of the sterilization bag into the sterilization chamber. The chamber is temperature-controlled and has a known air change and exchange rate. EtO is released from the cartridge until it is depleted, and the gas continues to diffuse into the sterilization chamber for the remainder of the sterilization cycle.

Forced air circulation in the aeration area is commonly used for load aeration and removal of residual EtO. Maintaining temperature uniformity and air re-circulation throughout the area is important, and these parameters should be monitored to ensure consistent and reproducible results. The aeration area should have airflow detection alarms or indicators on the air handling system to ensure that it is operating within specified parameters. Load temperature recording probes are used to monitor continuously the load during validation. The time of the load entry into, and removal from, the room area also is recorded.

The sterilization cycle is complete after the expiration of the set cycle time of at least about 4 hours. At that time, the amount of residual EtO gas molecules inside the gas diffusion bag and the sterilization chamber or room is small. Next, the purge cycle is started for the set cycle time of at least about 16 hours to remove and exhaust to the outside atmosphere all remaining EtO gas molecules from the device and needles, the bags, and the sterilization chamber prior to opening the sterilizer. The purge cycle is complete at the expiration of the set cycle time.

After completing the purge cycle, the sterilization bag containing the gas diffusion bags is removed from the sterilization chamber. The sterilization bag is opened to aid aeration of any residual gas. The cabinet door is immediately closed and re-purged. Sterilization monitoring devices or systems, such as biological and/or chemical indicators well-known to those skilled in the art are used to confirm that the sterilization parameters have been met.

Figure 4:
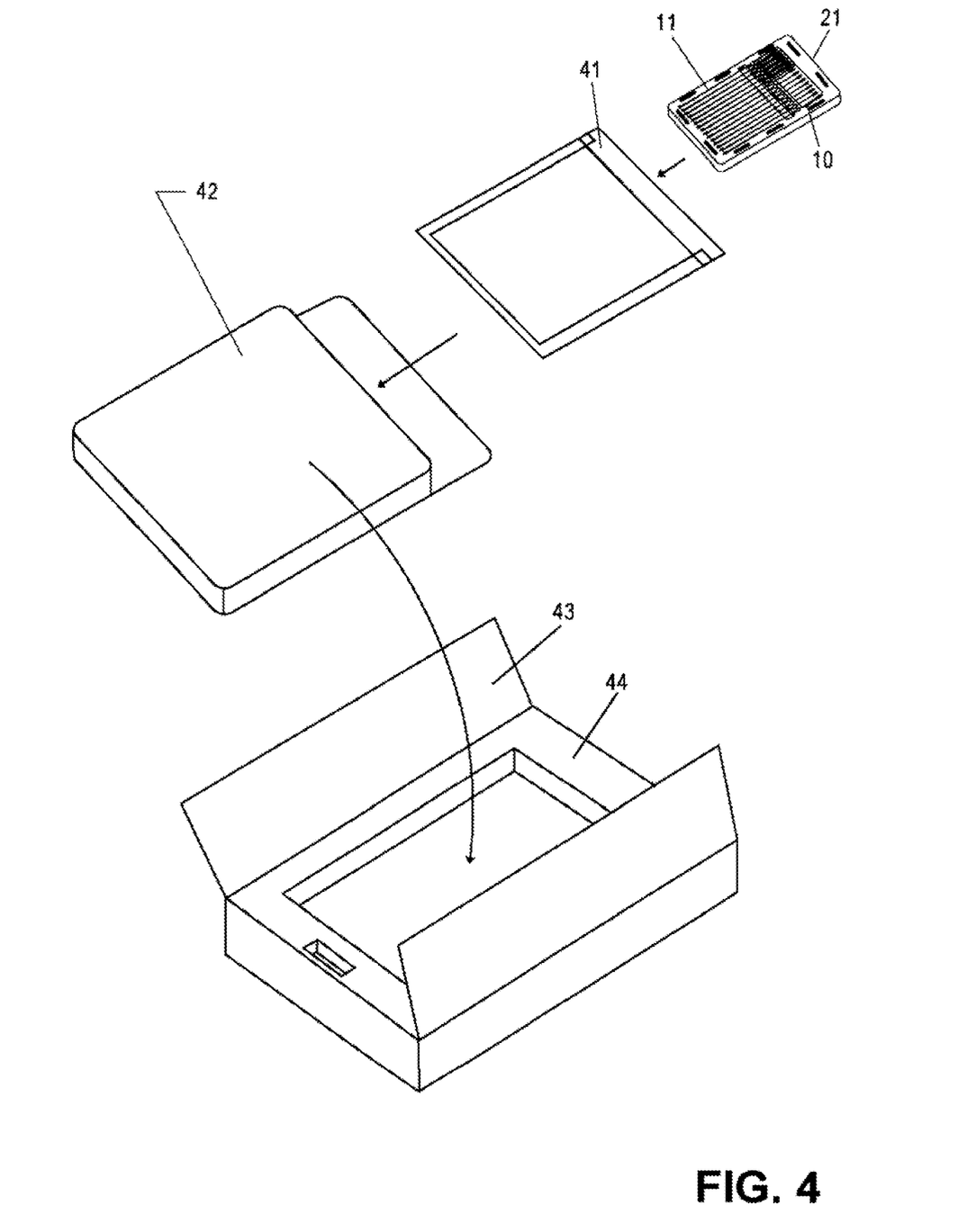
FIG. 4 shows a package configuration of how the sterilized product can be safely shipped.

Finally, once the cycle is complete and tray and its contents are sterile, the tray 21 (with the loaded needles 10) is sealed in a sterile pouch 41 to ensure continued sterility. See FIG. 4. The sterile pouch is then placed in a lead lined pouch to shield the radiation during transport to the hospital. A number of lead pouches can be placed in a box 43 with foam lining 44 for shipment to the treatment site.

Establishing the Critical Physical Parameters for Parametric Release

Before the products sterilized using the process set forth above can be routinely released on parametric release, the critical parameters for the process first must be established through physical and microbiological studies. The FDA has adopted the guidelines set in ANSI/AMMI/ISO 11135:1994 entitled "Medical Devices—Validation and Control of Ethylene Oxide Sterilization," for the parametric release of EtO-sterilized products. ANSI/AAMI/ISO 11135:1994 requires that for parametric release, critical parameters including humidity, EtO concentration, and lethality be established for both validation and routine cycles.

The ANSI/AAMI/ISO 11135:1994 standard for EtO sterilization has embraced two methods for establishing the critical parameters utilizing Process Challenge Devices ("PCD"). The first ("Method A") consists of an enumeration or physical count of microbe survivors in the BI, and the second ("Method B") measures the growth of the culture during fractional cycles. Under both methods, PCDs are prepared by placing a BI challenge in the most-difficult-to-sterilize location of the PCD using organisms of a known population and resistance. In the implants disclosed, these would include the inside of the needles and the surface of the radioactive seeds. The PCDs should be exposed to process parameters that provide less lethality than the proposed production process. The parameter data recorded during these studies is then used to determine the minimum production process and load parameters. The production process parameters will be equal to or greater than those employed during the process development studies. For each fractional cycle, all process parameters should remain constant with the exception of time.

Method A consists of exposing the inoculated PCDs to EtO exposure times of varying lengths, removing the BIs from the PCDs, and counting (i.e., enumerating) the number of surviving microorganisms on each BI. Five or more graded EtO exposure times must be performed. For the performance of this method to be acceptable, all of the exposure times used should result in recoverable populations. Exposure times should be chosen such that they are evenly-spaced, starting with zero and with the longest time producing a remaining population of 1 to 100 organisms per sample. The advantage of using Method A is that, in providing point-to-point values, the enumeration data can better predict the slope of the survivor curve using fewer studies to establish the curve shape. The major deficiency of this method is the difficulty in recovering survivors at lower counts.

Method B requires using sets of PCDs in a minimum of seven fractional cycles that apply graded exposures to EtO with all parameters, except time remains constant. The time intervals for this study should be of equal increments. Method B is easier to perform because it consists of sterility testing the BIs for pass/fail results, instead of enumerating the surviving microorganisms. Following exposure to fractional cycles with graded time increments, the BIs or inoculated carriers are removed from the PCD and tested for sterility. For this method to be useful in calculating the D-value, the sterility test must result in fractional growth of the sterility test samples (i.e., some positive and some negative). The drawback to this method is it is less accurate than Method A in calculating the final D-value. Additionally, more fractional cycles are required to support Method B than Method A.

Regardless of the method used to determine lethality, it is assumed that the organism population is homogeneous; the process parameters, with the exception of time, are constant from run to run; and, a semi-logarithmic survivor curve will be produced.

Using the survivor curve data obtained from either Method A or Method B, the critical parameter values and the required minimum EtO gas exposure time are established. It should be ensured that all critical parametric release parameters and any deviations to the protocol are documented. One should declare that the process has or has not met the success criteria of the protocol, on the basis of the test results.

The critical parameters of an EtO sterilization cycle include temperature, pressure, humidity, EtO concentration, and gas dwell time. The measurement and documentation of humidity in conditioning, and EtO gas concentration during exposure require particular attention. The concentration of humidity and EtO in the chamber are typically calculated by measuring pressure change. In addition, the amount of EtO also can be verified by measuring weight change in the storage container as EtO is added to the chamber.

Exemplary critical parameter values for the sterilization process outlined above are:
- Pre-conditioning of the sterilization load shall be 35-85% relative humidity and 21-50° C. prior to sterilization.
- The relative humidity throughout the sterilization dwell shall be within 35-85%.
- Release of the ethylene oxide gas shall not exceed the specified tolerance of ±5%
- Transmission rate of the sterilization bag materials is within 1.35-1.85 mg/in$^2$/hr.
- Sterilization and aeration dwell temperature preferably should not exceed a 10° C. spread (after product temperature stabilizes at approximately 46°-55° C.) for a cycle time of at least 16 hours (not including aeration).

The sterilization process consistently should deliver all critical process parameters to each and every component contained within the sterilization load, to a degree that will ensure a $10^{-6}$ SAL without causing any detrimental effect to the device or its packaging.

Validation of the Sterilization Process

Once the parametric release parameters have been established, the process must be validated in compliance with the requirements of the normative portions of ANSI/AAMI/ISO 11135:1994. The following steps are required in the validation study:

I) Commissioning ("IQ/OQ"): Commissioning involves the generation, collection, and documentation of evidence demonstrating that the design specifications of the sterilizer and all ancillary equipment are appropriate for their intended use. Installation qualification ("IQ") studies involve obtaining and documenting evidence that equipment has been provided and installed in accordance with its specifications and that it functions within predetermined limits when operated in accordance with operational instructions. Operational qualification ("OQ") studies are performed according to a protocol and are intended to demonstrate that the equipment will consistently perform in the selected environment over all intended ranges, as set forth in the specification. OQ studies are performed without the product to be sterilized. All OQ studies should be completed and approved before proceeding with the phases of physical and microbiological qualification.

II) Performance qualification ("PQ")-Microbiological: After successfully completing Method A or Method B and calculating a minimum gas exposure time, performance qualification is performed in the loaded chamber to demonstrate the following for the specified load configuration: a) The cycle is effective in achieving the specified SAL; b) the required parameters are achieved at all monitored locations in the production load; and c) the cycle is reproducible.

III) Load Configuration: The combination of product type, packaging, load density, and configuration constitutes a sterilization parameter termed "Load Configuration." This parameter will be identified and documented before starting the parametric release validation. The critical relationship between the product, packaging, load density, and configuration, relative to the sterilizing environment, should be established during the validation and shown to be reproducible. This relationship data is used to create the load configuration parameter for routine, production cycle, and parametric release. The parameter must be verified and documented after each sterilization cycle.

EtO sterilization users who intend to vary or mix product types, packaging, load/pallet configurations, and densities must establish and validate the specific degree of variance acceptable for achieving the specified SAL and the maintainability of all sterilizing parameters throughout the modified load. For that reason, it is recommended not to mix the seed implants discussed herein with other product types for sterilization.

IV) Performance Qualification-Physical: Full-length sterilization cycles should be run with temperature, relative humidity ("RH"), and EtO sensors to verify reproducibility of the process and to assess the impact of the cycle on the product and packaging functionality and residue levels. This performance qualification may be done in actual production loads, with release of the loads contingent on verification of reproducibility and on BIs included in the load.

During the validation cycle studies, a gas concentration profile for the entire gas dwell period should be developed and assessed to determine how the gas concentration changes over the period. Finished devices that have been used to validate a parametric release process should be exposed to a sterilization process that the above studies or prior qualifications support as a full cycle. Until parametric release has been approved for that cycle, BIs should be used to release such loads, provided that the requirements of conventional release have been met.

Finally, re-validation must be performed to ensure that process changes have not occurred and to demonstrate that the original validation program remains effective. Minimally, a single revalidation study or cycle is performed on an annual basis. The revalidation study must be documented and should include, but is not be limited to, the following elements: a) a review of the chamber performance and engineering changes over the past year to ensure that the commissioning process is still valid, including a review of the annual empty chamber temperature profile study and the relative humidity profiles of the preconditioning areas; b) confirmation of the delivered SAL of the sterilization process through microbiological studies; and c) confirmation of the previously established and documented bioburden trends and resistance.

Validation should take place at least annually with all combinations being re-validated within two years. Elimination of routine sterility tests on finished products will only be valid on the successful demonstration that the sterility assurance system is fully robust and capable. To be certified for routine parametric release, conformity of the physical processing parameters to all specifications established during validation must be demonstrated. Product release is based on documented review of processing records, rather than on testing of product sterility or process challenge devices. Qualified individuals should perform such documentation reviews. Note that this discussion is limited to release of the devices as sterile. Testing of characteristics other than sterility, such as radiation levels, may be required after sterilization.

The benefits of releasing products on parametric release are many. Once validation of the process has been completed, use of parametric release can streamline the EtO sterilization process from initial inventory control checks, preconditioning, sterilization, and aeration, followed by direct shipment to distribution sites. Allowing a few hours for initial and final inventory control, and 16 hours total for preconditioning, sterilization, and aeration, it is possible for a product lot to enter and exit an EtO sterilization facility within about 24 hours—thus rivaling the turnaround times offered by other sterilization methods. Additional advantages of parametric release are less product handling and related damage. A load that is going to be released parametrically can be net wrapped by the manufacturer and processed without ever having a single carton removed or opened.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed is:

1. A method of sterilizing a brachytherapy device comprising the steps of:

assembling the brachytherapy device by loading a radioactive seed implant into a delivery needle;

arranging a gas permeable safety plug over a distal end of the delivery needle;

inserting a stylet into a proximal end of the needle so that a portion of the stylet extends out from the delivery needle;

positioning the brachytherapy device in a tray by securing the distal end of the delivery needle to the tray and securing the portion of the stylet to the tray so as to resist relative movement of the stylet and the delivery needle;

packaging the brachytherapy device and the tray in a gas permeable package;

exposing the brachytherapy device and the package to a sterilizing gas;

sterilizing the brachytherapy device using a set of process parameters that provide a prescribed level of sterilization; and parametrically releasing the brachytherapy device from the sterilization process.

2. The method of claim 1 wherein the sterilizing step further comprises using at least one of the process parameters selected from the group consisting of load configuration, temperature, pressure, time, and gas concentration.

3. The method of claim 1 wherein said radioactive seed implant is a radioactive seed strand.

4. The method of claim 1, the sterilizing step further comprising using ethylene oxide gas to sterilize the brachytherapy device.

5. The method of claim 1 including maintaining a temperature for the sterilization step between 45° C. and 55° C.

6. A method of sterilizing at least one brachytherapy device, comprising steps of:

providing an open, sealable diffusion bag to contain said at least one brachytherapy device;

receiving a tray including the at least one brachytherapy device comprising a radioactive seed implant arranged in a delivery needle and a stylet arranged at least partially in the delivery needle so that a portion of the stylet extends out from the delivery needle;

wherein the delivery needle is secured to the tray and the portion of the stylet is secured to the tray so as to resist relative movement of the stylet and the delivery needle;

placing said at least one brachytherapy device and said tray into an interior of the open diffusion bag;

evacuating air from the diffusion bag;

sealing the diffusion bag;

positioning the diffusion bag in a chamber of a sterilizer having a ventilation system for removal of an exhaust gas from the chamber;

providing a sterilizing atmosphere in the interior of the diffusion bag by releasing into the diffusion bag ethylene oxide gas at a concentration sufficient to act as a sterilant;

heating ethylene oxide gas to an appropriate temperature;

maintaining the temperature of the ethylene oxide gas for a sufficient time to sterilize the at least one brachytherapy device.

7. The method of claim 6, including the step of selecting the diffusion bag constructed of a material that allows ethylene oxide gas to outwardly diffuse from the diffusion bag.

8. The method of claim 6, including the step of selecting the diffusion bag constructed of a tear-resistant material.

9. The method of claim 6, including the step of selecting the diffusion bag constructed of low density polyethylene.

10. The method of claim 6, including the step of selecting the diffusion bag being hermetically-sealed to form a substantially leak-proof seal.

11. The method of claim 6, including the step of releasing the ethylene oxide into the diffusion bag by a delivery mechanism.

12. The method of claim 11, including the step of choosing the delivery mechanism to be a cartridge containing ethylene oxide.

13. The method of claim 12, wherein the method further includes remotely activating the cartridge to release ethylene oxide gas.

14. The method of claim 6, wherein the method further comprises maintaining the temperature of ethylene oxide at about 45° C. to about 55° C.

15. The method of claim 6, further comprising a step of purging residual ethylene oxide gas from the diffusion bag for a sufficient time.

16. The method of claim 15, wherein the purging step duration is about 16 hours to 24 hours.

17. A method of sterilizing a brachytherapy device, the method comprising:
providing a gas permeable tray to contain said brachytherapy device;
wherein said brachytherapy device comprises a radioactive seed implant arranged in a delivery needle and a stylet arranged at least partially in the delivery needle so that a portion of the stylet extends out from the delivery needle;
securing the delivery needle to the tray and the portion of the stylet to the tray so as to resist relative movement of the stylet and the delivery needle;
placing said tray into a sealable diffusion bag;
sealing the diffusion bag;
positioning the diffusion bag in a chamber of a sterilizer having a ventilation system for removal of an exhaust gas from the chamber;
providing a sterilizing atmosphere in the interior of the diffusion bag by releasing into the diffusion bag ethylene oxide at a concentration sufficient to act as a sterilant;
heating the ethylene oxide to an appropriate temperature;
maintaining the temperature of the ethylene oxide gas for a sufficient time to sterilize the brachytherapy device and to complete the sterilization process;
conducting a performance qualification of the sterilization process through physical and microbiological studies;
extracting from the performance qualification a set of physical process parameters, which will consistently yield the desired sterility assurance level when said set of physical process parameters are maintained;
maintaining, monitoring, and recording the physical process parameters through direct analysis during routine processing; and
repeating the sterilization process for subsequent brachytherapy devices and releasing the sterilized brachytherapy devices on parametric release.

18. The method of claim 17, wherein one of said physical process parameters is a load configuration.

19. The method of claim 17, wherein one of said physical process parameters is a sterilization temperature.

20. The method of claim 17, wherein one of said physical process parameters is a pressure in said chamber of the sterilizer.

21. The method of claim 17, wherein one of said physical process parameters is a cycle time for sterilization and purging.

22. The method of claim 17, wherein one of said physical process parameters is a gas concentration profile.

23. The method of claim 17, wherein the sterility assurance level is $10^{-6}$.

24. The method of claim 17, wherein the method includes selecting the diffusion bag to be constructed of a material that allows ethylene oxide outwardly to diffuse from the diffusion bag.

25. The method of claim 17, wherein the method includes selecting the diffusion bag to be constructed of a tear-resistant material.

26. The method of claim 17, wherein the method further includes selecting the diffusion bag to be constructed of low density polyethylene.

27. The method of claim 17, wherein the method includes selecting the diffusion bag to be hermetically-sealed to form a substantially leak-proof seal.

28. The method of claim 17, wherein the method includes releasing ethylene oxide into the diffusion bag by a delivery mechanism.

29. The method of claim 28, wherein the delivery mechanism is a cartridge containing ethylene oxide.

30. The method of claim 29, wherein the method further includes remotely activating the cartridge to release ethylene oxide gas.

31. The method of claim 17, further comprising maintaining the temperature of the ethylene oxide at about 45° C. to about 55° C.

32. The method of claim 17, further comprising a step of purging residual ethylene oxide gas from the diffusion bag for a sufficient time.

33. The method of claim 32, wherein the purging duration is about 16 to 24 hours.

34. A method of sterilizing a brachytherapy device, the method comprising:
receiving the brachytherapy device secured to a gas permeable tray, the brachytherapy device including a radioactive seed implant arranged in a delivery needle;
receiving a stylet for use with the brachytherapy device;
wherein the stylet is secured to the tray;
placing said tray into a sealable diffusion bag;
positioning the diffusion bag in a chamber of a sterilizer;
providing a sterilizing atmosphere in the interior of the diffusion bag by releasing ethylene oxide into the diffusion bag at a concentration sufficient to act as a sterilant;
sterilizing the brachytherapy device by controlling an environment of the chamber using a set of process parameters; and
parametrically releasing the at least one brachytherapy device from the sterilization process.

35. The method of claim 34, wherein:
the ethylene oxide is released into the diffusion bag by way of a cartridge containing ethylene oxide; and
the step of providing a sterilizing atmosphere further includes remotely activating the cartridge to release ethylene oxide gas.

36. The method of claim 34, further comprising after parametrically releasing the at least one brachytherapy device:
removing said tray from the diffusion bag;
placing said tray into a sterile pouch;
sealing said sterile pouch; and
placing said sterile pouch in a lead pouch to block radiation leakage.

37. The method of claim 34, further comprising:
pre-conditioning the environment of the chamber with air having a relative humidity within a range of 35-85% at a temperature within a range of 21-50° C.; and maintaining the relative humidity within a range of 35-85% while sterilizing;
wherein releasing ethylene oxide is maintained at a rate within a tolerance of +/−5%.

38. The method of claim 34, further comprising:

receiving a series of brachytherapy devices corresponding to a treatment program, each brachytherapy device secured to the gas permeable tray, each brachytherapy device including a radioactive seed implant corresponding to a portion of the treatment program arranged in a corresponding delivery needle; and receiving corresponding stylets for use with each of the brachytherapy devices;

wherein each stylet are secured to the tray.

39. The method of claim 34, wherein the stylet is received arranged at least partially in the delivery needle so that a portion of the stylet extends out from the delivery needle; and wherein the portion of the stylet is secured to the tray so as to resist relative movement of the stylet and the delivery needle.

* * * * *